United States Patent [19]

Thompson et al.

[11] Patent Number: 4,927,025
[45] Date of Patent: May 22, 1990

[54] CAST DECORATION KIT

[76] Inventors: Gregory E. Thompson, 1008 S. Grant; Paul V. Thompson, 416 E. Mitchell, both of, Marshall, Mo. 65340

[21] Appl. No.: 405,229

[22] Filed: Sep. 11, 1989

[51] Int. Cl.$^5$ .............................................. B65D 69/00
[52] U.S. Cl. ...................................... 206/575; 206/38; 206/223
[58] Field of Search ................. 206/38, 223, 440, 457, 206/575, 581, 224; 150/154; 224/901, 165

[56] References Cited

U.S. PATENT DOCUMENTS

| H 467 | 5/1988 | Gladden | 206/575 |
|---|---|---|---|
| Re. 28,289 | 12/1974 | Calkins | 224/901 |
| 2,939,242 | 6/1960 | Papadakis | 206/575 |
| 3,840,113 | 10/1974 | Bartleson | 206/575 |
| 3,897,587 | 7/1975 | Molner | 206/575 |
| 4,696,400 | 9/1987 | Warman | 206/575 |

Primary Examiner—David T. Fidei
Attorney, Agent, or Firm—Kokjer, Kircher, Bradley, Wharton, Bowman & Johnson

[57] ABSTRACT

A kit for maintaining and enhancing the appearance of a plaster type cast includes a fabric sleeve which can be used to cover the cast if it is soiled, a waterproof cover for use when bathing, a pen set for marking on the cast and a plurality of decorative articles that may be applied to the cast. All of the components are packaged in a clam shell plastic package which is divided into plural compartments for storage of the various parts of the kit.

17 Claims, 1 Drawing Sheet

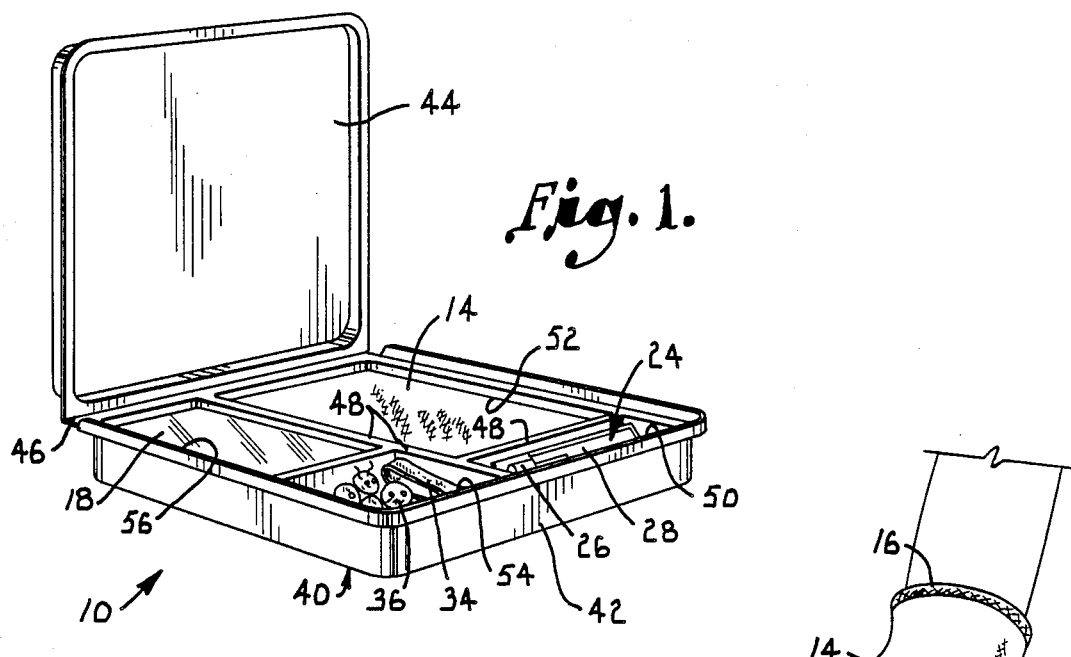
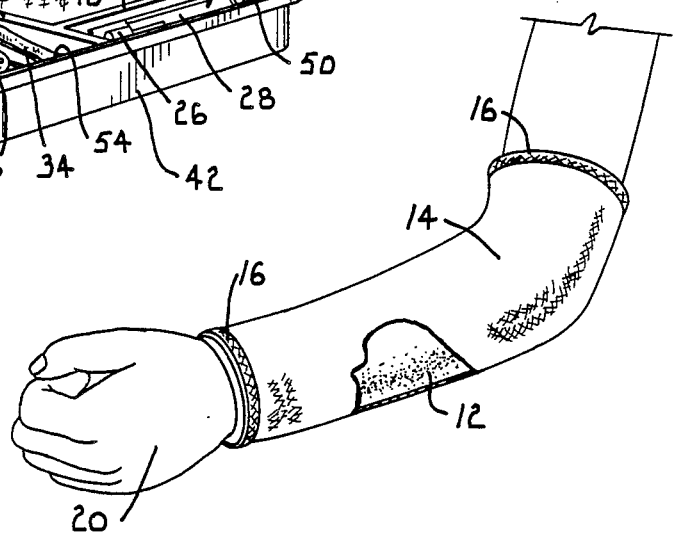
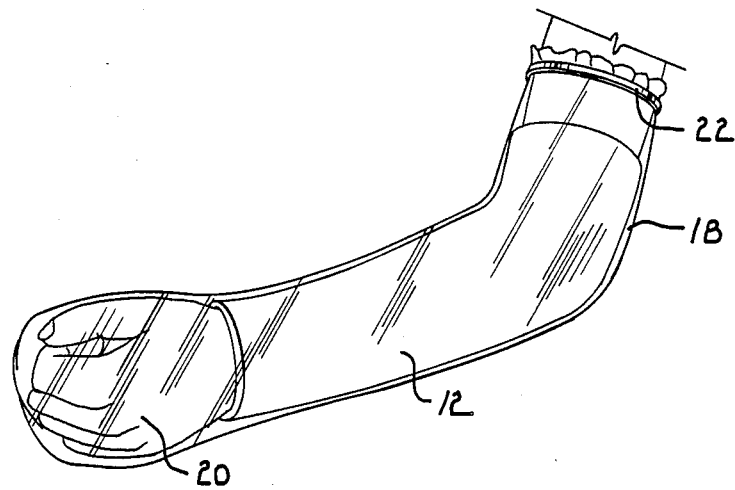
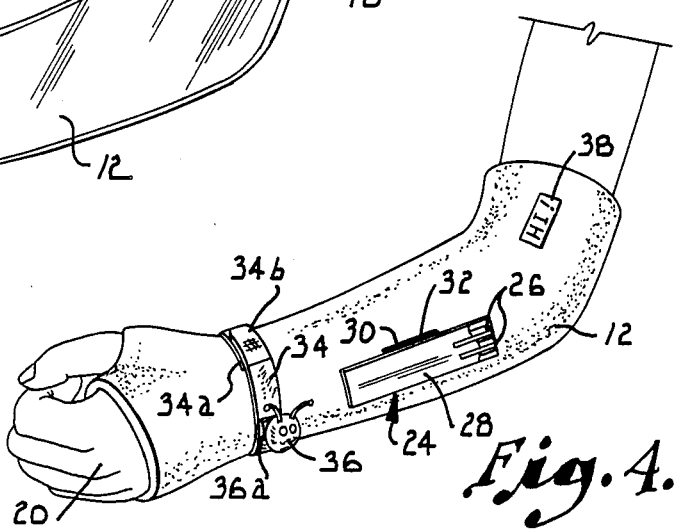

CAST DECORATION KIT

BACKGROUND AND SUMMARY OF THE INVENTION

This invention relates generally to plaster type casts and more particularly to a kit having a variety of components that are used to maintain and enhance the decorative appearance of a cast.

When bones such as those in the arms or legs are broken, they are normally set in a plaster type cast which provides immobilization while the bone heals. After the cast has been worn for some time, it usually becomes dirty and otherwise discolored and thus presents a rather poor appearance which is a particular problem when the wearer is in a public place. Keeping the cast and adjacent portions of the body dry while bathing or showering is another problem. It is common, particularly among young persons, for casts to be autographed by friends and relatives, and this requires a pen or other marking instrument which may not always be readily available.

The present invention is directed an arrangement which provides, in kit form, a variety of items that are useful to enhance and maintain the appearance of a plaster type cast. It is a particular feature of the invention that the various articles are furnished together in a kit which functions as a package as well as a storage box for the articles.

In accordance with the invention, a clam shell type plastic package has a compartmented base section and a hinged lid. Packaged in the different compartments are an attractive fabric sleeve which may be used to cover the cast when it is soiled, a waterproof plastic cover which can be applied over the cast and held in place by an elastic band to shield the cast from moisture during bathing, washing or showering, a pen set which can be attached to the cast so that markers are available for signing or otherwise marking on the cast, and a variety of decorative items such as bands, stickers, small characters such as animals or cartoon characters and other fanciful decorations. The kit thus provides a unitary package which contains a variety of articles that are useful with the cast both alone and in conjunction with other articles. Those articles in the kit which are not in use can be detached from the cast and conveniently stored in their respective compartments where they are readily available if needed.

DESCRIPTION OF THE DRAWINGS

In the accompanying drawings which form a part of the specification and are to be read in conjunction therewith and in which like reference numerals are used to indicate like parts in the various views:

FIG. 1 is a perspective view of a cast decoration kit constructed according to a preferred embodiment of the present invention, with the lid of the kit package open in order to expose the articles contained in the kit;

FIG. 2 is a perspective view showing the fabric sleeve included in the kit applied to a plaster arm cast, with a portion of the sleeve broken away for purposes of illustration;

FIG. 3 is a perspective view showing the waterproof cover included in the kit applied to an arm cast; and FIG. 4 is a perspective view showing the pen set and various decorative items included in the kit applied to a plaster arm cast.

DETAILED DESCRIPTION OF THE INVENTION

Referring now to the drawings in more detail and initially to FIG. 1, numeral 10 generally designates a cast decoration kit constructed in accordance with the present invention. The kit 10 includes a variety of items which are used with a plaster type cast such as the arm cast identified by numeral 12 in FIGS. 2-4.

With reference now to FIG. 2 in particular, the kit 10 includes a fabric sleeve 14 which may be applied as a cover for the cast 12 in the manner shown in FIG. 2. The sleeve 14 may be constructed of any suitable fabric and is preferably an attractive flexible fabric such as the synthetic type of fabric that is commercially available under the trademark SPANDEX. The sleeve 14 may be any suitable color, and it is large enough to completely cover the cast 12 in order to shield the cast from visibility when it becomes soiled, discolored, or otherwise unsightly. The fabric of which the sleeve 14 is constructed is preferably somewhat stretchable and elastic. Elastic bands 16 extend around the open opposite ends of the sleeve 14 and serve to retain the sleeve in place covering the cast. The fabric sleeve 14 can quickly and easily be applied to and removed from the cast 12.

FIG. 3 illustrates a waterproof plastic cover 18 which may be applied to cover the cast 12 as well as the hand 20. The cover 18 may be constructed of any suitable plastic which is flexible enough to be fitted over the cast 12 and which is water impenetrable. One end of the cover 18 is closed, while an elastic band 22 preferably extends around the open opposite end in order to secure the cover 18 in place on the arm in a manner to completely enclose the cast 12 and adjacent portions of the arm and wrist. The cover 18 may be but need not be a clear plastic substance.

Referring now to FIG. 4 in particular, the kit 10 also includes a pen set which is generally identified by numeral 24 and which includes a pair of marking pens 26 carried in a suitable case 28. The marking pens 26 are preferably felt type marking pens having different colors, and the bodies of the pens fit inside of the case 28 with the clips of the pens clipped onto the edge of the case in order to hold the pens in place.

The pen case 28 may be detachably secured on the surface of the cast 12 by means of a suitable connection. The connection may be established by mating patches 30 and 32, with the patch 30 being adhesively secured to the surface of cast 12 and the other patch 32 being secured to the back of the pen case 28. The facing surfaces of the patches 30 and 32 are provided with mating hook and loop type fasteners or some other suitable type of fasteners. It is noted that the case 28 can be detached from the cast 12 simply by pulling it off of the patch 30. Similarly, either of the marking pens 26 can be removed from the case simply by pulling them out.

With continued reference to FIG. 4, the kit 10 also includes various types of decorative items such as a wrist band 34, a fanciful character 36 and a sticker 38. The band 34 is long enough to extend around the circumference of the cast 12, with its opposite ends 34a and 34b overlapping. The overlapping ends 34a and 34b are preferably provided with mating hook and loop type fasteners or some other fastening means that is able to detachably secure the band 34 in extension around the cast 12. The fanciful character 36 may take virtually any desired form such as a small animal or a cartoon character. The character 36 may also be attached to the cast 12 in any suitable manner. For example a patch 36a to which the character 36 is secured may mate with the outer surface of band 34, such as by means of mating hook and loop type fasteners. In this manner, the character 36 may be applied to the band 34 and thus mounted on the cast 12 and it may likewise be easily detached from the cast. It should be understood that the character 36 may be mounted on a sticker which can be adhesively attached to the cast.

The sticker 38 may be of any size, and it typically includes a written message, artwork or some other type of visual depiction on its outer surface. The sticker may be adhesively attached to the surface of the cast 12 at any desired location, or it may be attached to the cast by some other means.

It is a particular feature of the invention that the kit 10 includes all of the components described above and that the components are packaged together in a single package which is generally identified by numeral 40 in FIG. 1. The package 40 is preferably a clam shell plastic package having an open topped base 42 and a lid 44 which is hinged to the base 42 by an integral hinge connection 46. The base 42 is a rectangular box like structure which is divided into a plurality of different compartments by suitable partitions 48. The partitions 48 divide the interior of the base 42 into four different compartments. One of the compartments is identified by numeral 50 and is a rectangular compartment having a size and shape to closely receive the pen set 24, including the case 28 with the two pens therein. A second compartment 52 which is formed in the base 42 is a rectangular compartment which receives the fabric sleeve 14. The sleeve 14 is suitably folded so that it fits easily within the compartment 52. A third compartment 54 is a square compartment in which the decorative items such as the band 34, character 36 and sticker 38 are contained, along with various other types of decorative articles. The fourth and last compartment 56 in the base 42 is a rectangular compartment that contains the waterproof cover 18. Preferably, the cover 18 is folded up such that it easily fits in the compartment 56.

The kit 10 is provided for retail sale with the pen set 24 packaged in compartment 50, the fabric sleeve 14 packaged in compartment 52, the decorative articles packaged in compartment 54 and the waterproof cover 18 along with its securing band packaged in compartment 56. The lid 44 is initially closed and sealed closed to cover the top of the base 42 and thus cover all of the compartments in the base to enclose the contents of the base. The lid 44 can be opened and closed about the hinge 46. When opened, the open top of the base 42 is exposed so that all of the compartments are accessible from the top in order to remove and replace components. Each component of the kit 10 can be removed from its compartment and applied to the cast 12 in the manner described previously. When not in use, each component can be removed from the cast and replaced in its respective compartment where it is conveniently stored and is readily available when needed. The package 40 thus serves both as a means for packaging the components of kit 10 as well as a storage box in which the components of the kit may be stored when not in use.

It should be noted that the various components of the kit can be applied to the cast alone or together with other of the components. For example, the various decorative articles can be applied either directly to the surface of the cast 12 or to the sleeve 14 if the sleeve is in place on the cast. Likewise the waterproof cover can be applied over the sleeve 14 if desired. The decorative articles may be applied as desired to the cast in order to decorate it in a personalized, customized fashion in accordance with the desires of the person wearing the cast. The pen set can be applied at any desired location to the cast 12 in order to make the marking pens 26 readily available for use by friends or relatives who want to autograph or otherwise mark on the surface of the cast 12.

Although the cast 12 is shown as an arm cast for purposes of illustration, it should be understood that the kit of the present invention is applicable to casts applied to legs or other parts of the body as well as to the arms. The fabric sleeve 14 and cover 18 can be provided in various sizes in order to be applicable to casts that are applied to different parts of the body.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. A kit for use with a cast said kit comprising:
   a marking instrument adapted to mark on the cast;
   an instrument holder for releaseably receiving said marking instrument and having means for attaching said holder detachably to the cast;
   a decorative fabric sleeve having a size and shape to closely cover the cast to enhance the appearance thereof;
   a plurality of decorative articles applicable to the cast to decorate same; and
   a package in which said decorative articles, said fabric sleeve, said instrument holder and said marking instrument are all contained.

2. The kit of claim 1, including:
   a waterproof cover having a size to cover the cast; and
   means for releaseably securing said cover over the cast in covering relationship thereto, said cover and securing means being contained in said package.

3. The kit of claim 2, wherein said package comprises:
   a base having a size and shape to receive and store said decorative articles, said fabric sleeve, said instrument holder with the instrument therein, said cover and said securing means; and
   a lid fitting on said base in a manner to open and close same.

4. The kit of claim 3, wherein said base in compartmented.

5. The kit of claim 3, wherein:
   said base presents a first compartment therein for holding said fabric sleeve;
   said base presents a second compartment therein for holding said instrument holder with the marking instrument therein;

said base presents a third compartment for holding said decorative articles; and said base presents a fourth compartment for holding said waterproof cover and securing means.

6. The kit of claim 5, wherein said lid of the package has a hinge connection with said base.

7. The kit of claim 1, wherein said package presents a plurality of different compartments therein, one of said compartments having a size and shape to contain said fabric sleeve, another compartment having a size and shape to contain said decorative articles, and yet another compartment having a size and shape to contain said instrument holder with said marking instrument therein.

8. The kit of claim 7, wherein said package comprises:
a base presenting said compartments therein; and
a lid fitting on said base in a manner to open and close same.

9. The kit of claim 8, wherein said lid of the package has a hinge connection with said base.

10. A kit for use with a cast, said kit comprising:
a package having a plurality of compartments therein separated from one another;
a marking instrument for marking on the cast;
an instrument case for releaseably receiving said marking instrument and having means for attaching said case with detachably to the cast, said case with the instrument therein being packaged in one of said compartments and being storable in said one compartment when detached from the cast;
a decorative fabric sleeve applicable to the cast to provide a covering therefor which enhances the appearance of the cast, said sleeve being packaged in a second compartment in the package and being foldable for storage in said second compartment when removed from the cast; and
a plurality of decorative articles applicable to the cast to decorate same, said articles being packaged in a third compartment in the package and being storable in said third compartment when removed from the cast.

11. The kit of claim 10, including a waterproof cover removably applicable to the cast in a manner to cover the latter and shield the cast from moisture, said cover being packaged in a fourth compartment in the package and being foldable for storage therein when removed from the cast.

12. The kit of claim 11, wherein said package comprises:
a base presenting said compartments therein; and
a lid fitting on said base in a manner to open and close same.

13. The kit of claim 12, wherein said lid has a hinge connection with said base.

14. The kit of claim 10, wherein said package comprises:
a base presenting said compartments therein; and
a lid fitting on said base in a manner to open and close same.

15. The kit of claim 14, wherein said lid has a hinge connection with said base.

16. A kit for use with a cast, aid kit comprising:
a package having an open top base and a lid movable between open and closed positions to open and close the top of the base, said base being divided into four separate compartments each accessible from the top of the base when the lid is open and each enclosed when the lid is closed;
a marking instrument for marking on the cast;
an instrument case for releaseably receiving and holding said marking instrument and having means for attaching said case detachable to the cast, said case with said instrument therein being packaged in a first one of said four compartments and being storable therein when detached from the cast;
a decorative fabric sleeve applicable to the cast to provide a covering therefor which enhances the appearance of the cast, said sleeve being packaged in a second one of said compartments and being foldable for storage therein when removed from the cast;
a plurality of decorative articles applicable to the cast to decorate same, said articles being packaged in a third one of said compartments and being individually storable therein when detached from the cast; and
a waterproof cover removably applicable to the cast to provide a waterproof shield therefore, said cover being packaged in the fourth compartment and being foldable for storage therein when removed from the cast.

17. The kit of claim 16, wherein said lid has a hinge connection with said base.

* * * * *